United States Patent [19]
Bussmann et al.

[11] Patent Number: 5,665,215
[45] Date of Patent: Sep. 9, 1997

[54] METHOD AND APPARATUS FOR MAKING PREDETERMINED EVENTS WITH A BIOSENSOR

[75] Inventors: Stephan A. Bussmann, Granger; Joseph E. Ruggiero, Goshen; Christine G. Trippel, Mishawaka, all of Ind.

[73] Assignee: Bayer Corporation, Elkhart, Ind.

[21] Appl. No.: 533,158

[22] Filed: Sep. 25, 1995

[51] Int. Cl.⁶ .................................... G01N 27/26
[52] U.S. Cl. .................. 204/403; 204/406; 204/407; 205/777.5; 422/82.02; 435/286.1; 435/287.1; 435/817
[58] Field of Search .................. 204/403, 406, 204/407; 205/777.5, 778; 422/82.02; 435/817, 288, 291, 289

[56] References Cited

U.S. PATENT DOCUMENTS

| | | | |
|---|---|---|---|
| 4,151,845 | 5/1979 | Clemens | 128/214 E |
| 4,407,959 | 10/1983 | Tsuji et al. | 435/288 |
| 4,685,059 | 8/1987 | Yamamoto | 364/415 |
| 4,731,726 | 3/1988 | Allen, III | 364/416 |
| 4,961,158 | 10/1990 | Sussman | 364/709.04 |
| 5,019,974 | 5/1991 | Beckers | 364/413.02 |
| 5,025,374 | 6/1991 | Roizen et al. | 364/413.02 |
| 5,053,199 | 10/1991 | Keiser et al. | 422/82.02 |
| 5,438,271 | 8/1995 | White et al. | 204/406 |

*Primary Examiner*—Bruce F. Bell
*Attorney, Agent, or Firm*—Jerome L. Jeffers

[57] ABSTRACT

A method and apparatus are provided for marking predetermined events with a biosensor. The biosensor includes a sensor for receiving a user sample to be measured and a processor for performing a predefined test sequence for measuring a predefined parameter value. A memory is coupled to said processor for storing predefined parameter data values. A marker member is manually coupled by the user to the processor for selectively marking one of a plurality of predetermined events with a stored predefined parameter data value.

10 Claims, 9 Drawing Sheets

METHOD AND APPARATUS FOR MAKING PREDETERMINED EVENTS WITH A BIOSENSOR

FIELD OF THE INVENTION

The present invention generally relates to a biosensor, and, more particularly, to a new and improved method and apparatus for marking predetermined events with a biosensor.

DESCRIPTION OF THE PRIOR ART

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets. While the remainder of the disclosure herein will be directed towards the determination of glucose, it is to be understood that the procedure and apparatus of this invention can be used for the determination of other analytes upon selection of the appropriate enzyme.

The ideal diagnostic device or biosensor for the detection of glucose in fluids must be simple, so as not to require a high degree of technical skill on the part of the patient or user administering the test. The biosensor also should be a rugged device providing reliable and repeatable operations and be economical to manufacture. The need for a keyboard or multiple key switches for entering patient data with the biosensor advantageously would be minimized or eliminated.

SUMMARY OF THE INVENTION

Important objects of the present invention are to provide a new and improved method and apparatus for marking predetermined events with a biosensor; to provide such method and apparatus that eliminates or minimizes the need for key switches; and to provide such method and apparatus that overcome many of the disadvantages of prior art arrangements.

In brief, a method and apparatus are provided for marking predetermined events with a biosensor. The biosensor includes a sensor for receiving a user sample to be measured and a processor for performing a predefined test sequence for measuring a predefined parameter value. A memory is coupled to said processor for storing predefined parameter data values. A marker member is manually coupled by the user to the processor for selectively marking one of a plurality of predetermined events with a stored predefined parameter data value.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
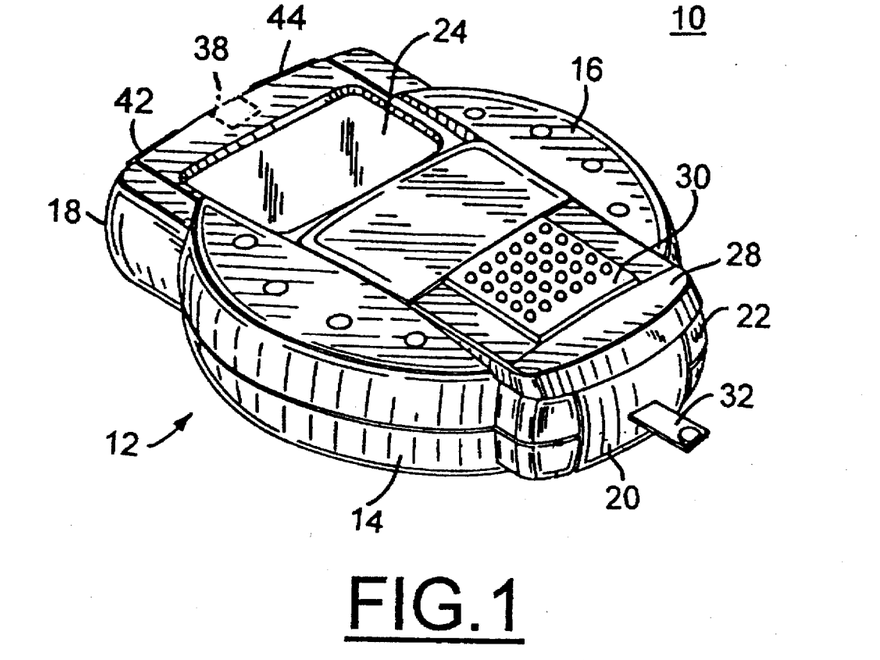
FIG. 1 is an enlarged perspective view of a biosensor shown in an open position in accordance with the present invention.
Figure 2:
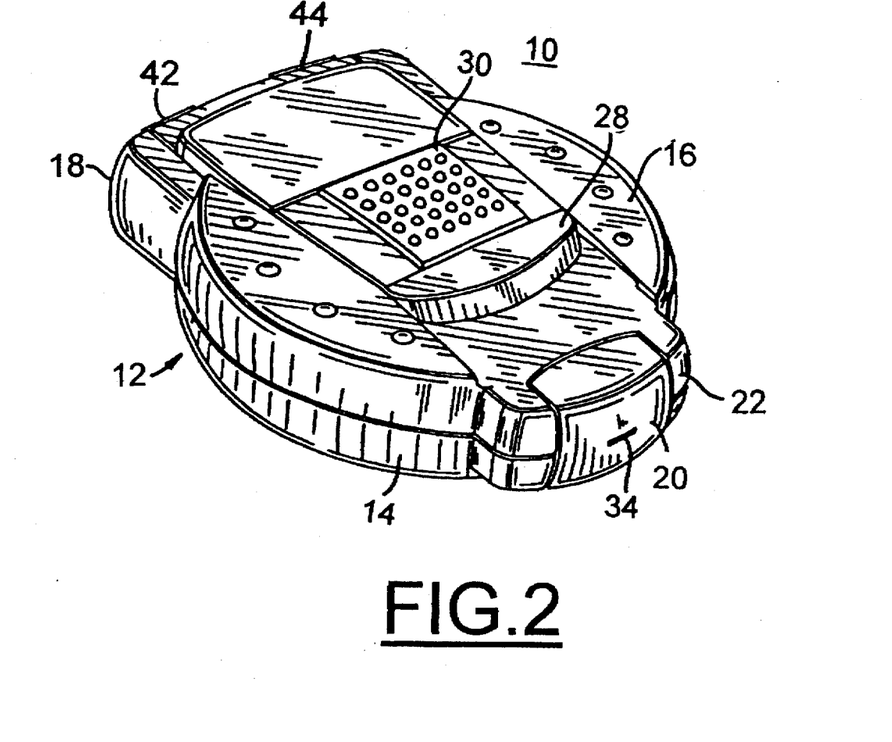
FIG. 2 is an enlarged perspective view of the biosensor of FIG. 1 shown in a closed position.

Having reference now to the drawings, in FIGS. 1 and 2 there is illustrated a biosensor designated as a whole by the reference character 10 and arranged in accordance with principles of the present invention. Biosensor 10 includes a clam-shell type enclosure 12 formed by a base member 14 and a cover member 16. Base and cover members 14 and 16 are pivotably attached together at a first end 18 and are secured together by a latch member 20 at a second, opposite end 22. A display 24, such as a liquid crystal display (LCD) is carried by the cover member 16. To turn the biosensor 10 on and off, a manually movable slide 28 mounted on the cover member 16 is moved between an open position shown in FIG. 1 and a closed position shown in FIG. 2.

In the closed or OFF position of FIG. 2, the slide 28 covers the display 24. A thumb grip 30 carried by the slide 28 is arranged for manual engagement by a user of the biosensor 10 to select the ON and OFF positions. The thumb grip 30 also is movable from left to right in the OFF position of slide 28 for selecting a system test operational mode. When a user moves the slide 28 to the ON position of FIG. 1, the display is uncovered and a sensor 32 is presented. The sensor 32 extends through a slot 34 and is positioned outside the enclosure 12 for the user to apply a blood drop. A right button 42 and a left button or switch 44 are carried by the enclosure 12 for operation by a user to set, recall and delete blood glucose readings and to set date, time, and options, respectively.

Figure 3:
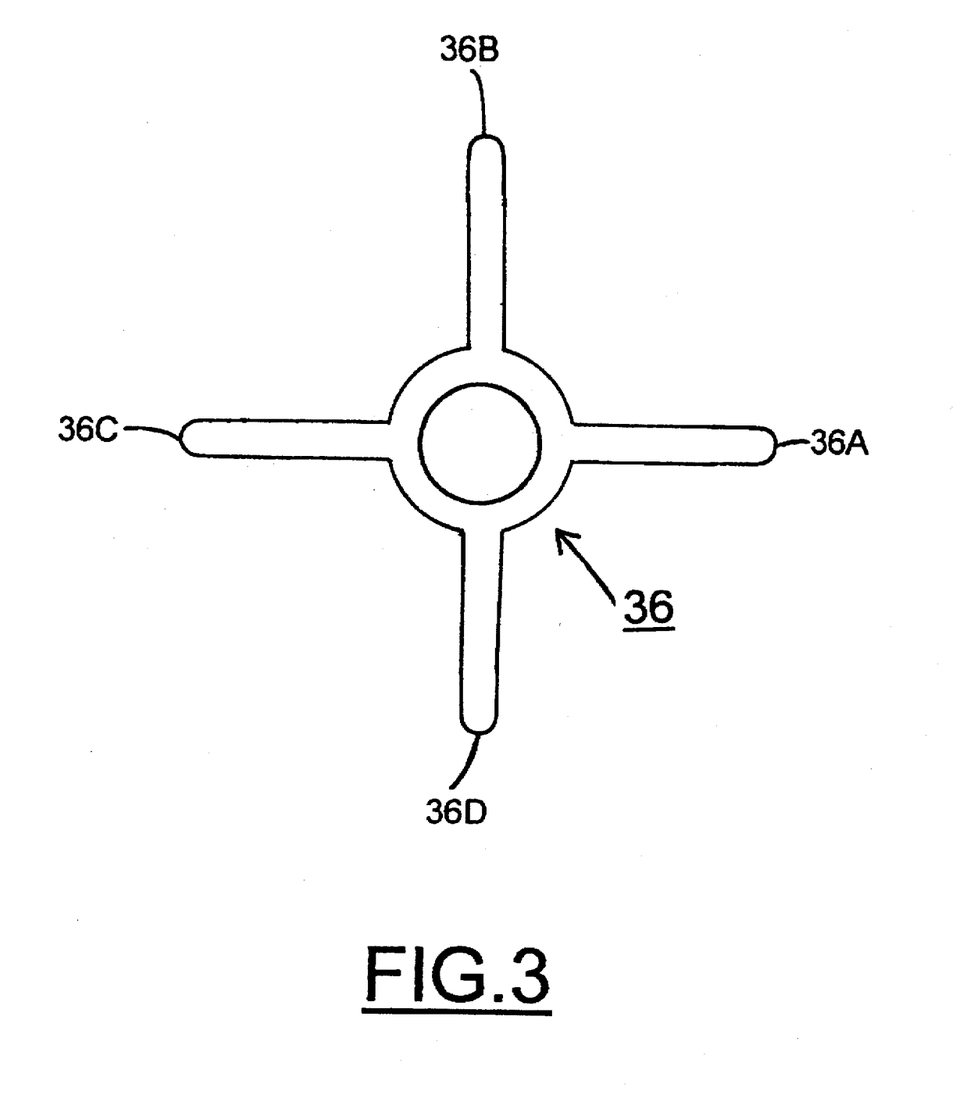
FIG. 3 is a plan view of a biosensor marking ring member in accordance with the present invention.

Referring also to FIG. 3, there is shown an exemplary marker member generally designated by the reference character 36 of the invention. Marker member 36 includes a plurality of spokes 36A, 36B, 36C and 36D for manual insertion of one of the spokes into an input aperture 38 to selectively mark a plurality of predetermined events. For example, blood glucose tests can be marked by the user for pre/post meal and other predefined events by inserting a selected one of the spokes 36A, 36B, 36C and 36D into the biosensor input 34 or data port 38. Each of the spokes 36A, 36B, 36C and 36D has a different predefined measured value, such as a different resistance value. The resistance value of the user selected, inserted spoke is identified to mark a particular, corresponding predetermined event. Marker member 36 can be stored within the enclosure 12 when not being used.

It should be understood that various different configurations can be provided for the marker member 36 instead of the ring configuration with multiple spokes or arms 36A, 36B, 36C and 36D, as shown. For example, a different number of arms 36A, 36B, 36C and 36D can be provided and each of the arms 36A, 36B, 36C and 36D can have a different length and/or color code and can carrying printed indicia for instructing the user. Instead of a ring configuration for the marker member 36, various structures can be used, for example, a clip.

Figure 4:
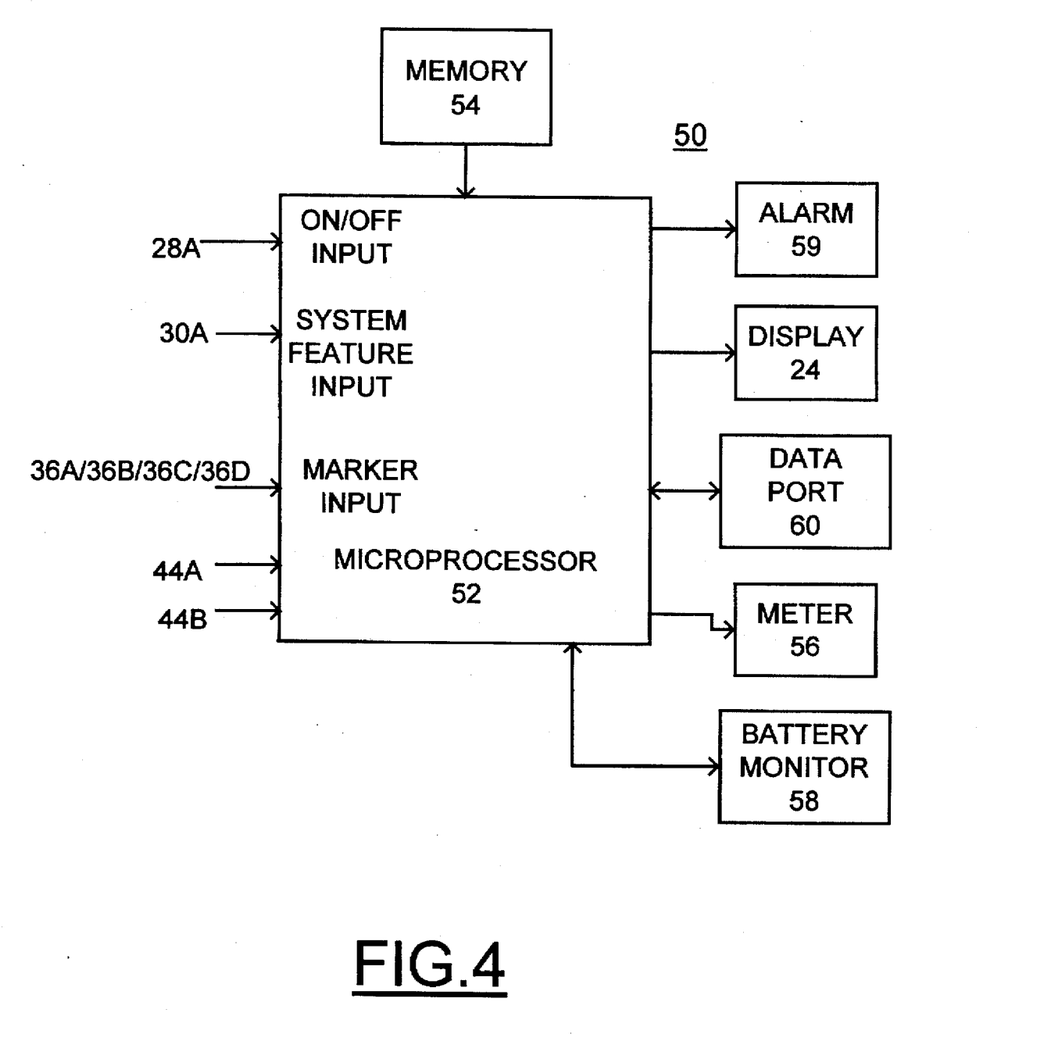
FIG. 4 is a block diagram illustrating biosensor circuitry of the biosensor of FIG. 1.

Referring also to FIG. 4, there is shown a block diagram representation of biosensor circuitry designated as a whole by the reference character 50 and arranged in accordance with principles of the present invention. Biosensor circuitry 50 includes a microprocessor 52 together with an associated memory 54 for storing program and user data. Microprocessor 52 contains suitable programming to perform the methods of the invention as illustrated in FIGS. 5, 6, 7, 8, 9A, and 9B. A meter function 56 coupled to sensor 32 is operatively controlled by the microprocessor 52 for recording blood glucose test values. A battery monitor function 58 is coupled to the microprocessor 52 for detecting a dead battery (not shown) condition. A data port or communications interface 60 couples data to and from a connected computer (not shown).

An ON/OFF input at a line 28A responsive to the user ON/OFF operation of the slide 28 is coupled to the microprocessor 52 for performing the blood test sequence mode of biosensor 10. A system features input at a line 30A responsive to the user operation of the thumb grip 30 is coupled to the microprocessor 52 for selectively performing the system features mode of biosensor 10. A predetermined event marker input at a line 36A/36B/36C/36D is coupled to the microprocessor 52 for performing the predetermined event marking feature of biosensor 10. User push-button responsive inputs at a pair of lines 42A and 44A from the push-button switches 42 and 44 are applied to the microprocessor 52 to set, recall and delete blood glucose readings and to set date, time, and biosensor options.

Figure 5:
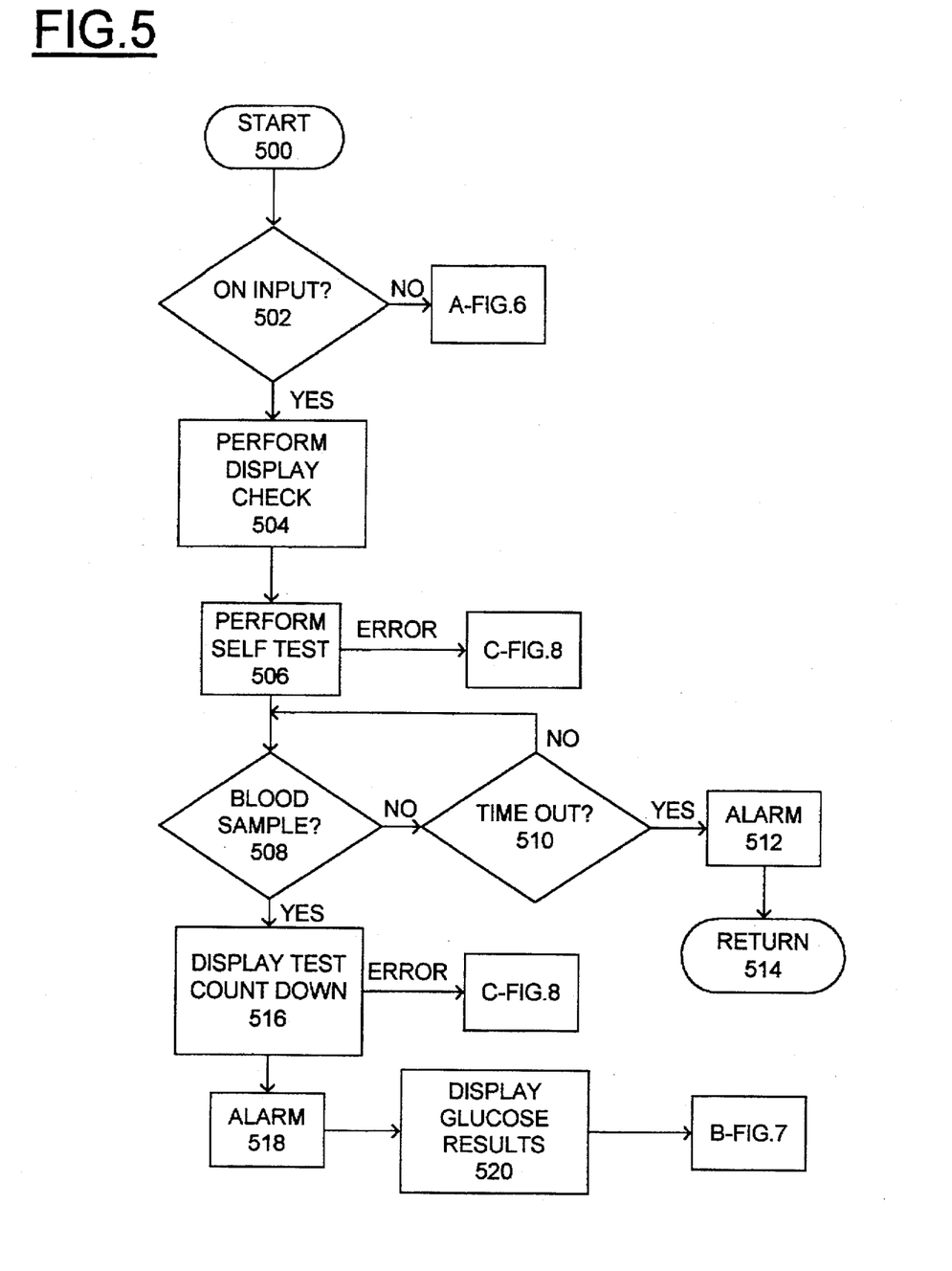
FIGS. 5, 6, 7, 8, 9A and 9B are flow charts illustrating logical steps performed by the biosensor of FIG. 1.

Referring now to FIG. 5, there is shown a flow chart illustrating sequential steps beginning at a block 500 that are performed by the microprocessor 52 of the biosensor 10. An ON input at line 28A is identified as indicated at a decision block 502. Otherwise, a system features input at line 30A is identified at block 600 following entry point A in FIG. 6. After the meter is initially turned on by moving the slide 28 forward with the thumb grip 30 to the right, as shown in FIGS. 1 and 2, microprocessor 52 performs a display check as indicated at a block 504 and performs a meter self-test as indicated at a block 506. When an error is identified at either of the blocks 504 and 506, then the sequential operations continue following entry point C in FIG. 8.

After the meter self-test and display check, the biosensor 10 displays a blood drop symbol to prompt the user to apply a blood sample to the sensor 32 that was presented responsive to moving slide 28 forward to the ON position. Checking for a blood sample is provided as indicated at a decision block 508. Biosensor 10 will wait for a predetermined time period, for example fifteen minutes for the user to apply a blood sample before a meter time-out occurs as indicated at a decision block 510. This time-out period allows ample time for the user to apply a blood sample to the sensor 32 and limits the exposure time of sensor 32 to the environment to ensure that the sensor does not deteriorate during the test sequence. When the time-out period has elapsed, then an alarm can be sounded as indicated at a block 512. Then the biosensor will turn OFF automatically if a blood sample has not been applied to the sensor 32 and the sequential operations return to the start as indicated at a block 514.

Otherwise, when the user applies a blood sample to the sensor 32 that is identified at block 508, then the biosensor 10 will display a predefined test countdown, for example a thirty second countdown as indicated at a block 516. When an error is identified at block 516, then the sequential operations continue following entry point C in FIG. 8. When the countdown is completed, biosensor 10 will sound an alarm, such as for one second, if enabled, as indicated at a block 518. Then biosensor 10 will display the glucose test results as indicated at a block 520. Then sequential operation continue following entry point B in FIG. 7.

Figure 6:
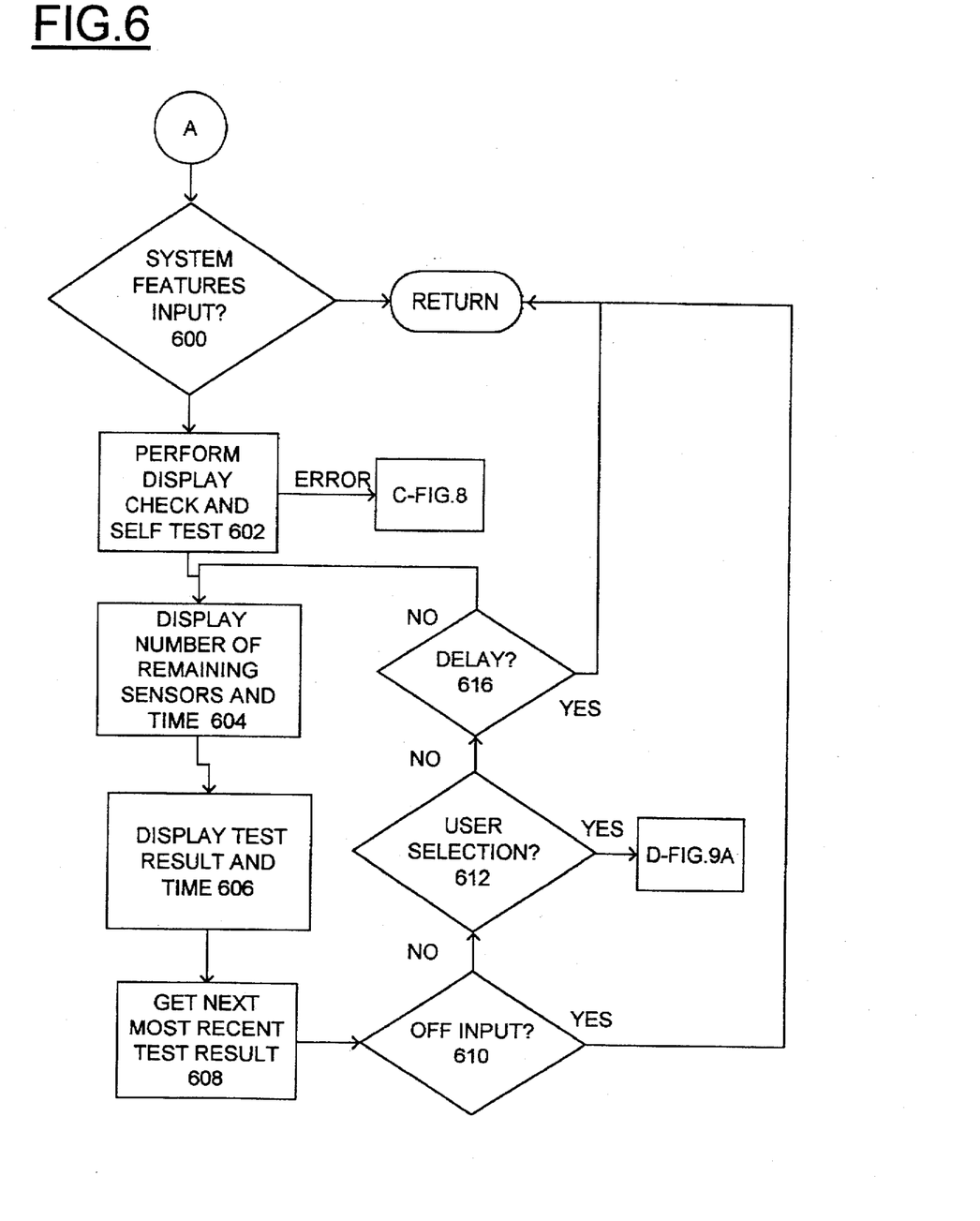

Referring now to FIG. 6, the system features mode is entered by the user moving the thumb grip 30 to the left position and moving the slide 28 forward that is identified at the decision block 600. Biosensor 10 initiates a display check and self test as indicated at a block 602. When an error is identified at block 602, then the sequential operations continue following entry point C in FIG. 8. After the meter self-test has been completed, biosensor 10 displays a number of remaining sensors that are contained within the housing 12 together with displaying the time as indicated at a block 604. Following the meter display of the number of remaining sensors, biosensor displays the most recent test result together with the time as indicated at a block 606. The next most recent test result is loaded as indicated at a block 608. The user can turn the meter OFF at any time and the sequential steps return as indicated at a decision block 610. Biosensor 10 identifies a user selection as indicated at a decision block 612. User selections identified at decision block 612 provide the system features modes illustrated in FIGS. 9A and 9B. Biosensor 10 continues to sequence through displaying the number of remaining sensors (block 604), the most recent test result (block 606), until the operator selects one of the system features modes (block 612), the operator turns OFF the meter (block 610), or a predefined delay, such as three minutes time-out occurs as indicated at a block 616.

Figure 7:
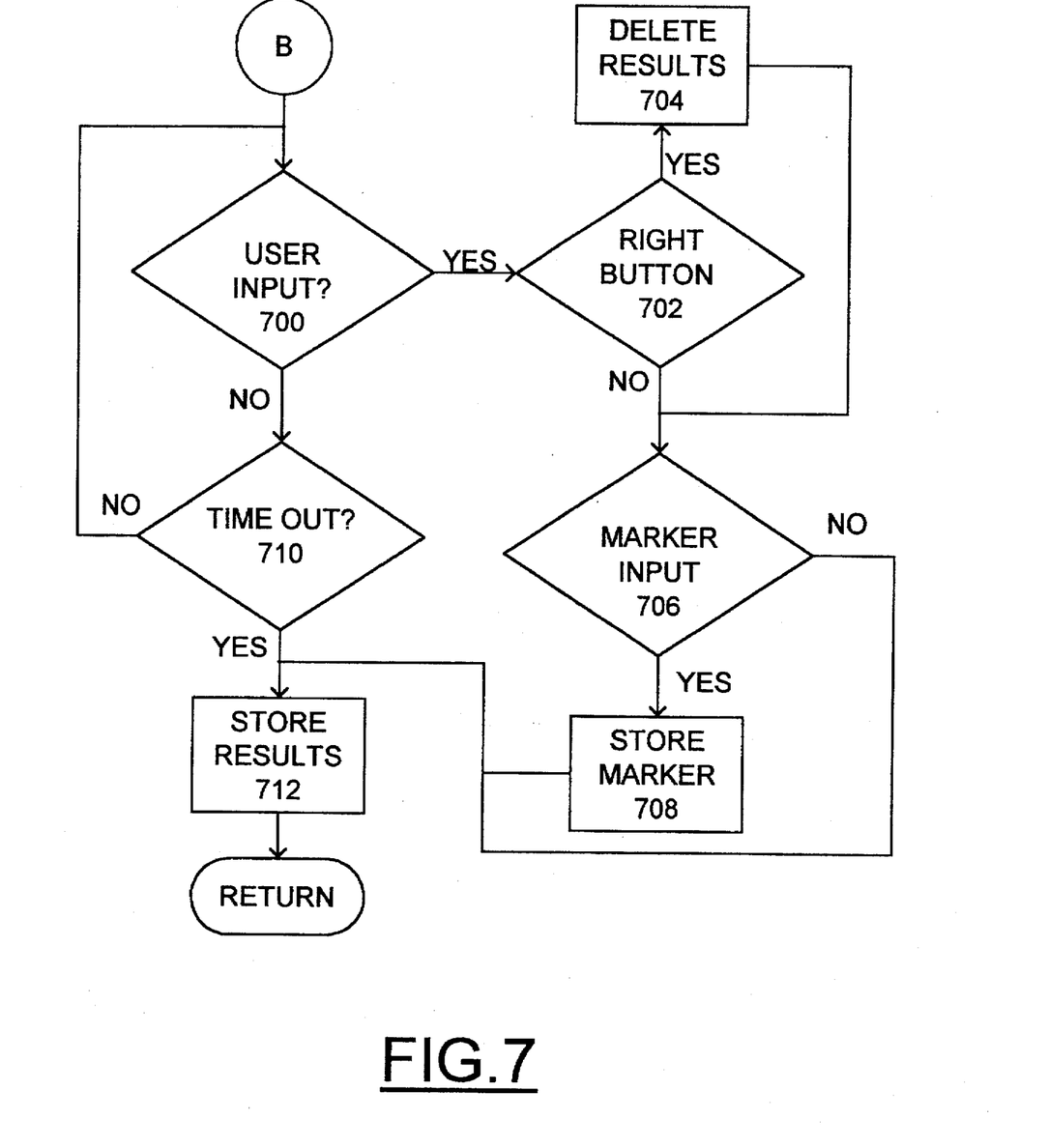

Referring now to FIG. 7, the sequential steps during a test sequence continue following entry point B with checking for a user input as indicated at a decision block 700. The user presses the right button 42 to delete the glucose result just taken as indicated at block 702 and 704. A marker input is identified at a decision block 706. When the user selects to mark a predetermined event, a user selected one of the resistance values is applied to the microprocessor 52 by the user inserting one of the spokes 36A, 36B, 36C or 36D that is identified at the decision block 706. The identified marker value corresponding to the selected predetermined event is stored as indicated at a block 708. Then the glucose test results are stored as indicated at a block 712 to complete the test sequence.

Figure 8:
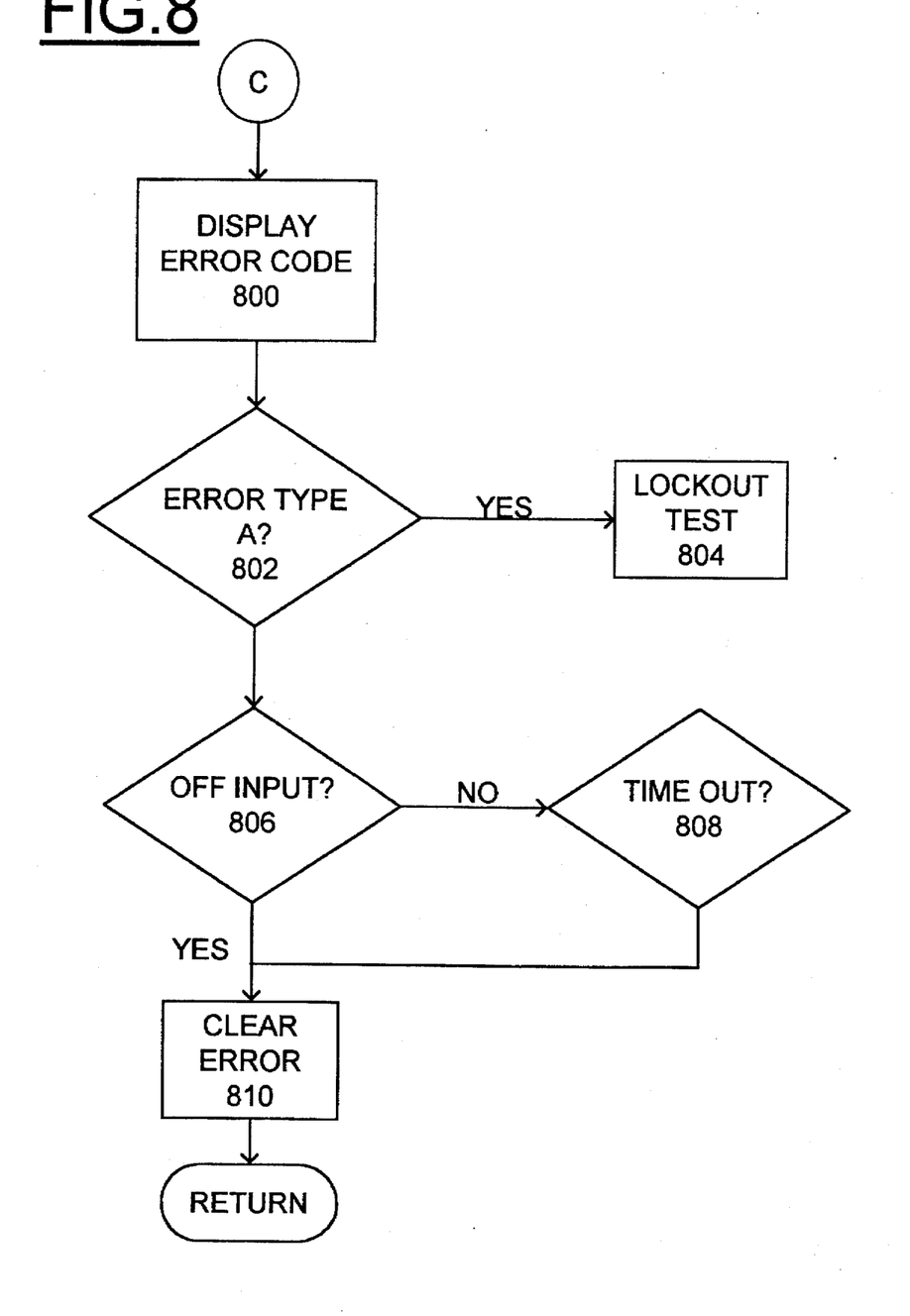

Referring now to FIG. 8, there are shown sequential steps performed following entry point C after an error condition is identified. First an error code is displayed for viewing by the user as indicated at a block 800. Next an error type and operations mode is identified at a decision block 802. For predetermined error types, a test lockout is provided in order to avoid possibly erroneous test results as indicated at a block 804. For example, when a dead battery is identified by battery monitor function 58, biosensor 10 is locked out from further operation until the dead batteries are replaced. An OFF input when the biosensor 10 is turned OFF by the user, is identified as indicated at a decision block 806. When an operator OFF input is not identified within a predefined time period as indicated at a decision block 808, then biosensor 10 turns itself off. The error is cleared when the operator turns OFF the biosensor 10 or when the meter turns itself OFF automatically after the predefined time period of inactivity as indicated at a block 810. This completes the error sequence.

Figure 9A:
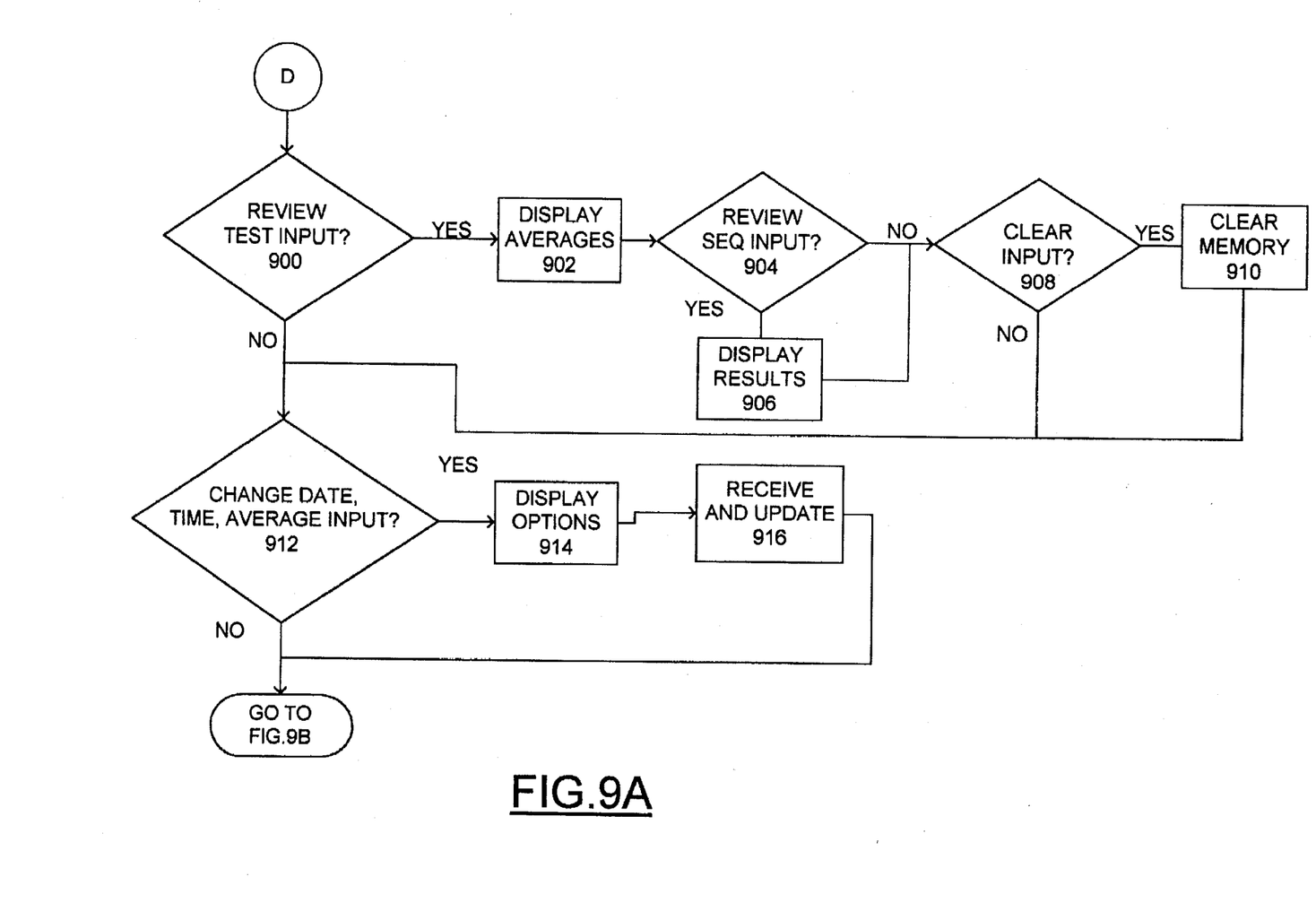
Figure 9B:
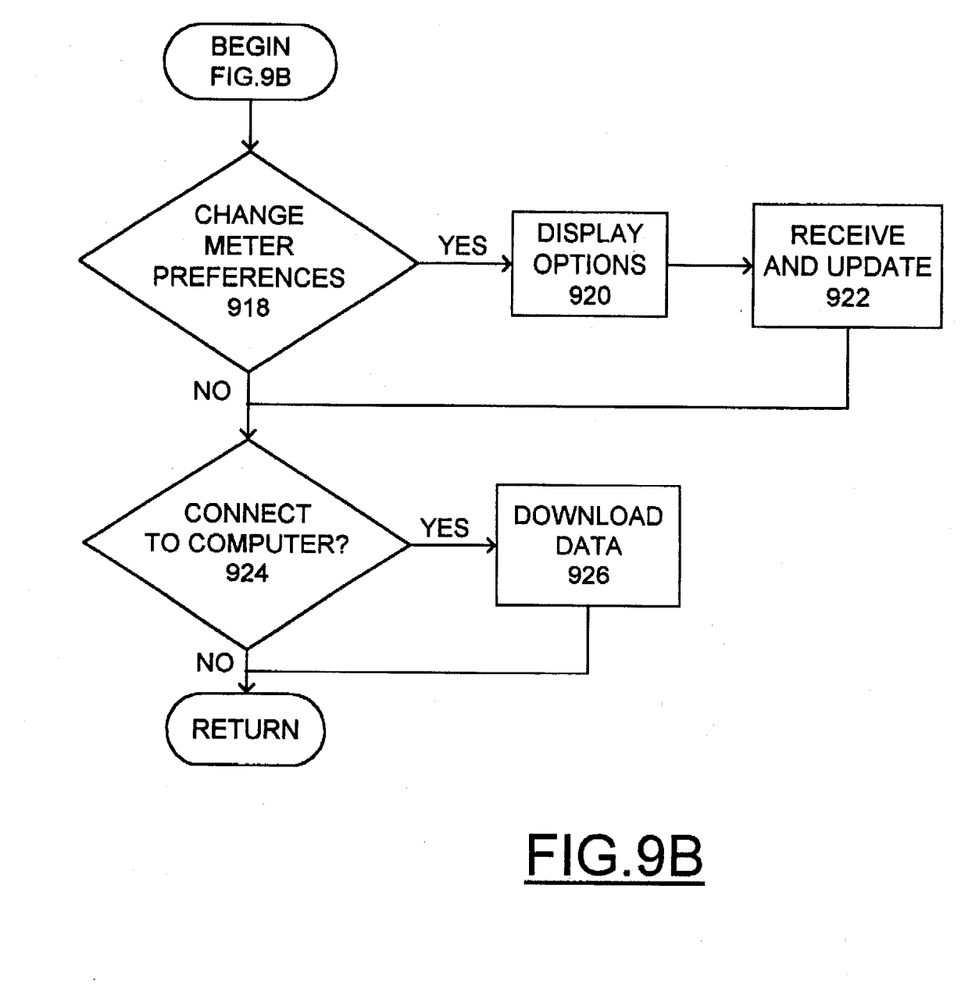

Referring now to FIGS. 9A and 9B, sequential steps responsive to an operator system features input selection are shown. An operator selection for reviewing previous test results is identified as indicated at a decision block 900. The biosensor 10 displays predetermined averages, for example the last two week average of glucose results that have not been deleted followed by other predefined averages of stored test results, as indicated at a block 902. Then a user's pressing of the right button 42 can be identified at a block 904 to sequence the biosensor 10 for displaying a next individual average or if all the individual averages have been displayed, then biosensor 10 displays the most recent test result performed at a block 906. A clear input selection applied by the user is identified as indicated at a decision block 908. The clear input selection is provided by the user pressing both the left and right buttons 42 and 44 for a predefined time period, for example five seconds. Then the memory is cleared as indicated at a block 910.

An operator's selection to change date, time, or average input is identified as indicated at a decision block 912. Biosensor 10 displays the current information or options, such as current time as indicated at a block 914 and the left button 44 is used to accept (store) the current information displayed and to select the next option (information) to be changed or edited at a block 916.

Having reference to FIG. 9B, an operator's selection to change meter preferences is identified as indicated at a decision block 918. Biosensor 10 displays the current options, such as an alarm enabled or disabled mode, as indicated at a block 920 and receives the user selected options and stores the changed options as indicated at a block 922.

A connect to a computer input is identified as indicated at a decision block 924. When the biosensor 10 detects that a computer (not shown) is connected, the biosensor enters a connect to a computer mode. Biosensor 10 sends a request to download result data signal out to download memory results to the connected computer. Biosensor receives an acknowledgment and downloads results data stored in the biosensor's memory 54 to the connected computer as indicated at a block 926.

While the present invention has been described with reference to the details of the embodiments of the invention shown in the drawings, these details are not intended to limit the scope of the invention as claimed in the appended claims.

What is claimed is:

1. A biosensor comprising:
   means for receiving a user sample;
   processor means responsive to said user sample receiving means for performing a test sequence for measuring a set parameter value;
   memory means coupled to said processor means for storing said set parameter data values;
   a marker member, said marker member being manually coupled by the user to said processor means for selectively marking one of a plurality of set events with a stored set parameter data value, said marker member including a plurality of different electrically measurable values corresponding to said plurality of set events.

2. A biosensor as recited in claim 1 wherein said marker member includes a plurality of different resistance values, one of said different resistance values being manually coupled by the user to said processor means for selectively marking one of a plurality of set events.

3. A biosensor as recited in claim 2 wherein said marker member includes a plurality of spokes and wherein each of said plurality of spokes applies a signal to said processor means corresponding to one of said set events.

4. A biosensor as recited in claim 3 wherein said each of said plurality of spokes contains a different resistance value.

5. A biosensor as recited in claim 1 further includes a housing and said housing including an aperture for slideably receiving said marker member that is manually inserted by the user into said aperture.

6. A biosensor as recited in claim 5 wherein said housing carries a slide member coupled to said processor means and manually movable by the user for selecting ON/OFF operational modes.

7. A biosensor as recited in claim 5 wherein said housing carries a switch coupled to said processor means and manually operated by the user for selecting operational characteristics for the biosensor.

8. A biosensor as recited in claim 1 wherein said processor means includes means for detecting an error condition and means responsive to a detected error condition for displaying a set corresponding error code.

9. A biosensor as recited in claim 1 wherein said processor means includes means for performing set system features operational modes responsive to a user selection.

10. A method for marking set events with a biosensor comprising the steps of:
   providing the biosensor with a sensor for receiving a user sample and a processor for performing a test sequence for measuring a predefined parameter value;
   providing a marker member including a plurality of different electrically measurable values; and
   selectively manually coupling one of said plurality of different electrically measurable values by the user to said processor for selectively marking one of a plurality of set events.

* * * * *